(12) United States Patent
Parekh et al.

(10) Patent No.: US 6,459,994 B1
(45) Date of Patent: Oct. 1, 2002

(54) METHODS FOR COMPUTER-ASSISTED ISOLATION OF PROTEINS

(75) Inventors: Rajesh Bhikhu Parekh, New Wendlebury; James Alexander Bruce, Long Hanborough; Robin Philp, Wantage, all of (GB); Lida H. Kimmel, Chester; David L. Friedman, Madison, both of CT (US)

(73) Assignee: Oxford GlycoSciences (UK) Ltd, Abingdon (GB)

(*) Notice: Subject to any disclaimer, the term of this patent is extended or adjusted under 35 U.S.C. 154(b) by 0 days.

(21) Appl. No.: 09/724,383

(22) Filed: Nov. 28, 2000

Related U.S. Application Data

(63) Continuation of application No. PCT/GB99/01742, filed on Jun. 1, 1999, now abandoned.

(30) Foreign Application Priority Data

May 29, 1998 (GB) .............................................. 9811656

(51) Int. Cl.[7] .............................................. G01N 33/48
(52) U.S. Cl. ............................ 702/19; 702/22; 702/27; 702/30
(58) Field of Search ............................ 702/19, 22, 27, 702/30; 382/129, 153, 128, 209, 294

(56) References Cited

U.S. PATENT DOCUMENTS

| | | |
|---|---|---|
| 3,499,360 A | 3/1970 | Davis |
| 4,221,533 A | 9/1980 | Heim et al. |
| 4,341,735 A | 7/1982 | Seifried |
| 4,592,089 A | 5/1986 | Hartman |
| 4,613,573 A | 9/1986 | Shibayama et al. |
| 4,684,613 A | 8/1987 | Barrere et al. |
| 5,073,963 A | 12/1991 | Sammons et al. |
| 5,098,539 A | 3/1992 | Shieh |
| 5,217,591 A | 6/1993 | Gombocz et al. |
| 5,275,710 A | 1/1994 | Gombocz et al. |
| 5,587,062 A | 12/1996 | Togawa et al. |
| 5,717,602 A | 2/1998 | Kenning |
| 5,949,899 A | 9/1999 | Ng |
| 5,993,627 A | 11/1999 | Anderson et al. |
| 6,064,754 A * | 5/2000 | Parekh et al. ................ 382/129 |
| 6,127,134 A | 10/2000 | Minden et al. |
| 6,278,794 B1 * | 8/2001 | Parekh et al. ................ 382/129 |

FOREIGN PATENT DOCUMENTS

| | | |
|---|---|---|
| DE | 30 32 069 A1 | 3/1982 |
| EP | 0 162 693 A2 | 11/1985 |
| EP | 0 119 090 B1 | 4/1987 |

(List continued on next page.)

OTHER PUBLICATIONS

Amess et al., *Electrophoresis*, 16:1255–1267 (1995).
Appel, *Proteome Research: New Frontiers in Functional Genomics*, pp 149–175 (1997).
Bigge et al., *Analytical Biochemistry*, 230:229–238 (1995).

(List continued on next page.)

*Primary Examiner*—John S. Hilten
*Assistant Examiner*—Hien Vo
(74) *Attorney, Agent, or Firm*—Klauber & Jackson; Valeta A. Gregg

(57) ABSTRACT

The present invention is directed to efficient, computer-assisted methods and apparatus for identifying, selecting and characterizing biomolecules in a biological sample. According to the invention, a biological sample is first treated to isolate biomolecules of interest, and a two-dimensional array is then generated by separating the biomolecules present in a complex mixture. The invention provides a computer-generated digital profile representing the identity and relative abundance of a plurality of biomolecules detected in the two-dimensional array, thereby permitting computer-mediated comparison of profiles from multiple biological samples. This automatable technology for screening biological samples and comparing their profiles permits rapid and efficient identification of individual biomolecules whose presence, absence or altered expression is associated with a disease or condition of interest.

19 Claims, 1 Drawing Sheet

FOREIGN PATENT DOCUMENTS

Figure 1:
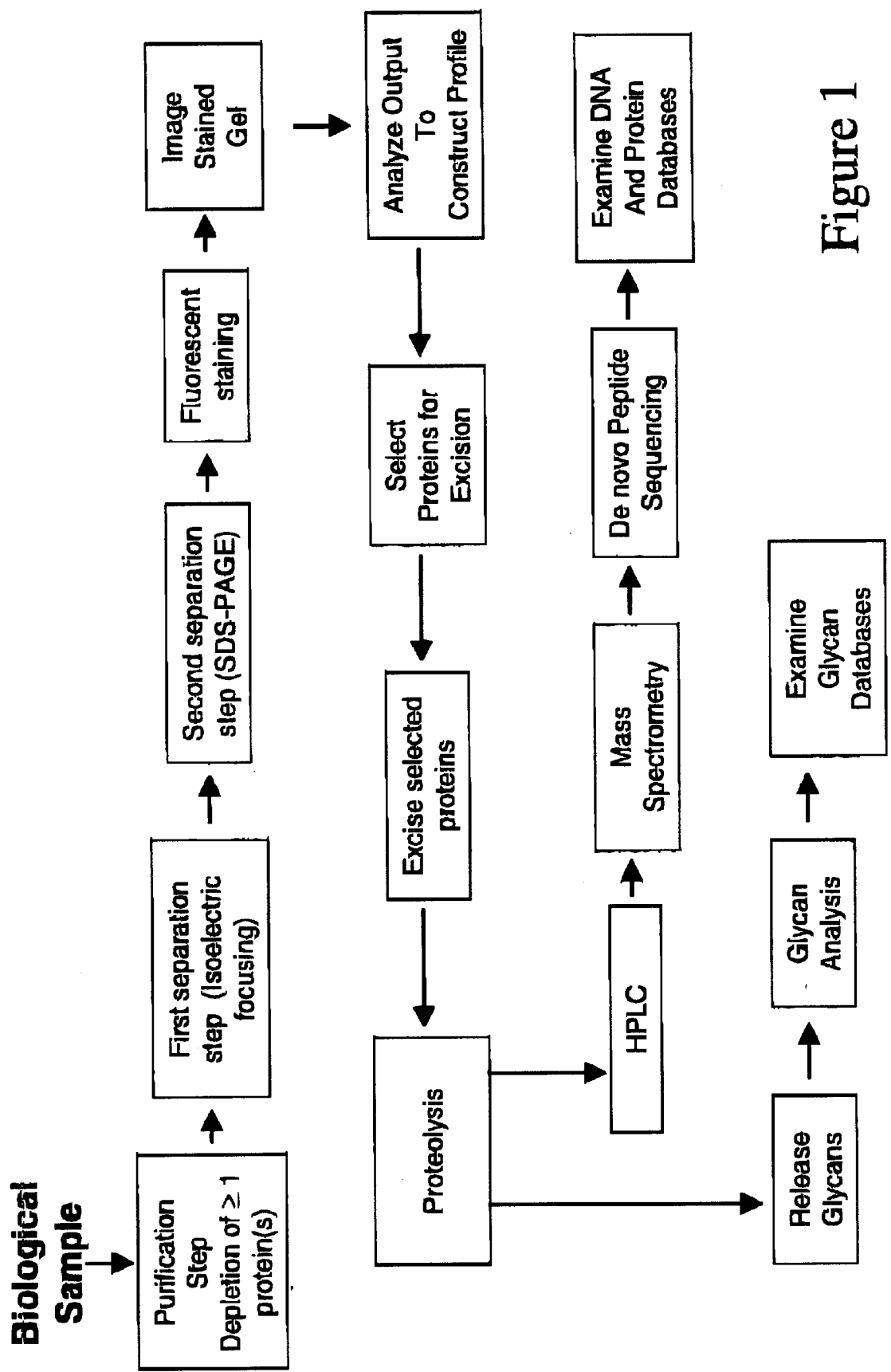

| | | |
|---|---|---|
| EP | 0 119 808 B1 | 4/1987 |
| EP | 0 126 638 B1 | 6/1988 |
| EP | 0 324 539 A2 | 1/1989 |
| EP | 0 163 472 B1 | 4/1991 |
| EP | 0 510 824 A1 | 4/1992 |
| EP | 0539 888 A1 | 5/1993 |
| EP | 0555 145 A2 | 8/1993 |
| EP | 0 806 659 A1 | 11/1997 |
| JP | 7-260742 | 10/1995 |
| WO | WO 93/05698 A1 | 4/1993 |
| WO | WO 93/15394 A1 | 8/1993 |
| WO | WO 95/14118 A1 | 5/1995 |
| WO | WO 95/22058 A1 | 8/1995 |
| WO | WO 96/18099 A1 | 6/1996 |
| WO | WO 96/18892 A1 | 6/1996 |
| WO | WO 96/33406 A1 | 10/1996 |
| WO | WO 96/39625 A1 | 12/1996 |
| WO | WO 97/26539 A1 | 7/1997 |
| WO | WO 98/19271 | 5/1998 |

OTHER PUBLICATIONS

Clauser et al., *Proc Natl Acad Sci USA*, 92:5072–5076 (1995).

Ducret et al., *Electrophoresis*, 17:866–879 (1996).

Eng et al., *J Am Soc Mass Spectrom*, 5:976–989 (1994).

Figeys et al., *Anal. Chem.*, 68(11):1822–1828 (1996).

Firestone et al., *Methods/ in Enzymology*, 182:688–699 (1990).

Gevaert et al., *Electrophoresis*, 17:918–924 (1996).

Gooley et al., *Proteome Research: New Frontiers in Functional Genomics*, pp 65–91 (1997).

Herbert et al., *Proteome Research: New Frontiers in Functional Genomics*, pp 13–33.

Hochstrasser, *Proteome Research: New Frontiers in Functional Genomics*, pp 187–219 (1997).

Hochstrasser, *Proteome Research: New Frontiers in Functional Genomics*, pp 233–237 (1997).

Houthaeve et al., *FEBS Letters*, 376:91–94 (1995).

Jensen et al., *Protein Structure: A Practical Approach*, pp 29–57 (1997).

Jones et al., *Nucleic Acids Research*, 20(17):4599–4606 (1992).

Lehrach et al., *Interdisciplinary Science Reviews*, 22(1):37–44 (1997).

Linn, *Methods in Enzymology*, 182:9–15 (1990).

Maier et al., *J. Biotechnology*, 35:191–203 (1994).

Medvick et al., *Laboratory Robotics and Automation*, 7:81–84 (1995).

Parekh et al., "Towards an Automated and Integrated Approach for the Molecular Characterisation of the Human Proteome," (Abstract), *Handbook of ICES meeting entitled "From Genome to Proteome"*, Siena, Sep. 16–18, 1996 (publication date unknown) (1996).

Patterson et al., *Electrophoresis*, 16:1791–1814 (1996).

Pharmacia Biotech, Immobiline® DryStrip kit for 2–D elecrophoresis with Immobiline® DryStrip and ExcelGel™ SDS, Instructions (Ref.18–1038–63, Edition AB) pp 1–36 (1994).

Phoretix, *Setting the Standard in 1D and 2D electrophoresis*, pp 1–15 (1997).

Radola, *Electrophoresis*, 1:43–56 (1980).

Sanchez et al., *Electrophoresis*, 18:324–327 (1997).

Shevchenko et al., *Analytical Chemistry*, 68(5):850–858 (1996).

Starr et al., *Journal of Chromatography A*, 720:295–321 (1996).

Takahashi, *Journal of Chromatography A*, 720:217–225 (1996).

Uber et al., *Biotechniques*, 11(5):642–647 (1991).

Westermeier, *Electrophoresis in Practice: A Guide to Theory and Practice*, pp 197–214 (1997).

Wilkins et al., *Proteome Research: New Frontiers in Functional Genomics*, pp 35–64 (1997).

Williams et al., *Proteome Research: New Frontiers in Functional Genomics*, pp 1–12 (1997).

Williams et al., *Proteome Research: New Frontiers in Functional Genomics*, pp 221–232 (1997).

Zakharov, *Applied and Theoretical Electrophoresis*, 5:25–29 (1995).

\* cited by examiner

METHODS FOR COMPUTER-ASSISTED ISOLATION OF PROTEINS

RELATED PATENT APPLICATIONS

This is a continuation application of PCT/GB99/01742, filed Jun. 1, 1999, (now abandoned), which claims priority under §119 to GB 9811656.9 filed May 29, 1998.

1. INTRODUCTION

This invention relates to computer-assisted methods and apparatus for efficiently and systematically studying molecules that are present in biological samples and determining their role in health and disease. In particular, this invention relates to the emerging field of proteomics, which involves the systematic identification and characterization of proteins that are present in biological samples, including proteins that are glycosylated or that exhibit other post-translational modifications. The proteomics approach offers great advantages for identifying proteins that are useful for diagnosis, prognosis, or monitoring response to therapy and in identifying protein targets for the prevention and treatment of disease.

2. BACKGROUND OF THE INVENTION

Recent advances in molecular genetics have revealed the benefits of high-throughput sequencing techniques and systematic strategies for studying nucleic acids expressed in a given cell or tissue. These advances have highlighted the need for operator-independent computer-mediated methods for identifying and selecting subsets or individual molecules from complex mixtures of proteins, oligosaccharides and other biomolecules and isolating such selected biomolecules for further analysis.

Strategies for target-driven drug discovery and rational drug design require identifying key cellular components, such as proteins, that are causally related to disease processes and the use of such components as targets for therapeutic intervention. However, present methods of analyzing biomolecules such as proteins are time consuming and expensive, and suffer from inefficiencies in detection, imaging, purification and analysis.

Though the genomics approach has advanced our understanding of the genetic basis of biological processes, it has significant limitations. First, the functions of products encoded by identified genes—and especially by partial cDNA sequences—are frequently unknown. Second, information about post-translational modifications of a protein can rarely be deduced from a knowledge of its gene sequence, and it is now apparent that a large proportion of proteins undergo post-translational modifications (such as glycosylation and phosphorylation) that can profoundly influence their biochemical properties. Third, protein expression is often subject to post-translational control, so that the cellular level of an mRNA does not necessarily correlate with the expression level of its gene product. Fourth, automated strategies for random sequencing of nucleic acids involve the analysis of large numbers of nucleic acid molecules prior to determining which, if any, show indicia of clinical or scientific significance.

For these reasons, there is a need to supplement genomic data by studying the patterns of protein and carbohydrate expression, and of post-translational modification generally, in a biological or disease process through direct analysis of proteins, oligosaccharides and other biomolecules. However, technical constraints have heretofore impeded the rapid, cost-effective, reproducible, systematic analysis of proteins and other biomolecules present in biological samples.

3. SUMMARY OF THE INVENTION

The present invention is directed to efficient, computer-assisted methods and apparatus for identifying, selecting and characterizing biomolecules in a biological sample. According to the invention, a biological sample is first treated to isolate biomolecules of interest, and a two-dimensional array is then generated by separating the biomolecules present in a complex mixture. The invention provides a computer-generated digital profile representing the identity and relative abundance of a plurality of biomolecules detected in the two-dimensional array, thereby permitting computer-mediated comparison of profiles from multiple biological samples. This automatable technology for screening biological samples and comparing their profiles permits rapid and efficient identification of individual biomolecules whose presence, absence or altered expression is associated with a disease or condition of interest. Such biomolecules are useful as therapeutic agents, as targets for therapeutic intervention, and as markers for diagnosis, prognosis, and evaluating response to treatment. This technology also permits rapid and efficient identification of sets of biomolecules whose pattern of expression is associated with a disease or condition of interest; such sets of biomolecules provide constellations of markers for diagnosis, prognosis, and evaluating response to treatment.

The high throughput, automatable methods and apparatus of the present invention further permit operator-independent selection of individual separated biomolecules (or subsets of separated biomolecules) according to pre-ordained criteria, without any requirement for knowledge of sequence information or other structural characteristics of the biomolecules. This in turn provides automated, operator-independent isolation and parallel characterization of a plurality of selected biomolecules detected in a biological sample. Thus, the present invention advantageously permits automated selection of biomolecules prior to sequencing or structural characterization.

3. BRIEF DESCRIPTION OF THE DRAWINGS

FIG. 1 is a flow diagram illustrating functions that are performed on a mixture of different proteins according to one embodiment of the invention.

4. DETAILED DESCRIPTION OF THE INVENTION

The present invention provides methods for rapidly and efficiently identifying and characterizing bio-molecules, for example proteins, in a biological sample. In a first step, a biological sample is treated to isolate the biomolecules of interest prior to separating the bio-molecules for characterisation. Purification is performed with a view either to selectively enrich certain desirable biomolecules, e.g. proteins, from within the sample or to selectively deplete the sample of certain undesirable biomolecules. For example, if glycosylated proteins only are of interest, such glycoproteins may be selectively isolated from a sample using lectin-affinity chromatography or lectin affinity precipitation. Such enrichment can both enhance and simplify the subsequent protein separation and analysis. Any proteins or group of proteins carrying a structural determinant for which an antibody or other specific purification reagent is available may be so extracted, e.g. tyrosine phospho-proteins by using an anti-phosphotyrosine antibody. Conversely, a sample may be depleted of specific proteins, again using protein-specific affinity methods. For example, albumin may be removed from body fluids using an anti-albumin antibody, and immunoglobulins may be removed using protein A or protein G (preferably immobilised) and haptoglobin and transferrin can be similarly removed. It is clear that a sample may be selectively depleted (or enriched) for more than one protein by using protein-specific reagents serially or in combination. Such enrichment/depletion can often have a beneficial effect during analysis, by concentrating proteins of interest/removing proteins that interfere with or may, for example by their predominance, limit the analysis of proteins of interest.

In either case of enrichment or depletion, the end result is to provide a sample containing the biomolecules of interest in a more isolated or "pure" form with respect to the original biological sample. A preferred method for achieving this is affinity chromatography e.g. Fast Protein Liquid Chromatography (FPLC).

After purification, the sample containing the biomolecules is subjected to two successive separation steps. In the first separation step, the biomolecules are separated according to one physical or chemical property so as to generate a one-dimensional array containing the biomolecules; for example, proteins are separated by isoelectric focusing along a first axis. In the second separation step, the biomolecules in this one-dimensional array are separated according to a second physical or chemical characteristic so as to generate a two-dimensional array of separated biomolecules; for example, proteins separated by isoelectric focusing are subjected to SDS-PAGE along a second axis perpendicular to the first axis. The separated biomolecules are stably maintained in the two-dimensional array for subsequent imaging. The stable two-dimensional array can be stored or archived for an extended period (e.g. months or years) and selected biomolecules can be retrieved from the array at any desired time, based on automated computer analysis of the data derived from imaging.

The two-dimensional array is imaged with a detector to generate a computer-readable output that contains a set of x,y coordinates and a signal value for each detected biomolecule. If desired, the computer-readable output can be displayed to a human operator—before or after computer-mediated analysis—as a computer-generated image on a screen or on any suitable medium. Computer-mediated analysis of the computer-readable output is performed, resulting in a computer-readable profile that represents, for a plurality of detected biomolecules, the relative abundance of each such biomolecule and its attributes as deduced from its x,y coordinates in the two-dimensional array. For example, a profile derived from imaging a gel containing proteins separated by isoelectric focusing followed by SDS-PAGE represents the isoelectric point (pI), apparent molecular weight (MW) and relative abundance of a plurality of detected proteins.

The computer-readable profiles of the present invention are suitable for computer-mediated analysis to identify one or more biomolecules that satisfy specified criteria. In one embodiment, a first set of profiles is compared with a second set of profiles to identify biomolecules that are represented in all the profiles of the first set (or in a first percentage of the profiles of the first set) and are absent from the profiles of the second set (or are absent from a second percentage of the profiles of the second set, where the first and second percentages can be independently specified). In other embodiments, sets of profiles are compared to identify biomolecules that are present at a designated higher level of expression in a specified percentage of profiles of one sample set than in a specified percentage of profiles of another sample set, or to identify biomolecules whose post-translational processing differs from one sample set to another.

One or more biomolecules so identified are selected for isolation. In one embodiment, this selection is made automatically by a computer, in accordance with pre-ordained programmed criteria, without further human intervention. In another embodiment, a human operator reviews the results of the computer-mediated analysis and then enters a selection into a computer. For isolation of each selected biomolecule, a computer generates machine-readable instructions that direct a robotic device (a) to remove one or more portions of the two-dimensional array that contain the selected biomolecule and (b) to deliver the removed portions to one or more suitable vessels for further characterization. For example, a selected protein can be analyzed to determine its full or partial amino acid sequence, to detect and characterize any associated oligosaccharide moieties, and to study other aspects of post-translational processing, e.g. phosphorylation, myristylation and the like. The invention advantageously permits automated parallel processing of biomolecules removed from the two-dimensional array, thereby facilitating rapid and efficient characterization of a plurality of selected biomolecules. FIG. 1 of WO-A-9823950 presents a flowchart illustrating processing of a sample.

The present invention is useful for identifying and analyzing proteins, but is more generally applicable to the identification and analysis of any biomolecule. As used herein, the term "biomolecule" refers to any organic molecule that is present in a biological sample, and includes peptides, polypeptides, proteins, oligosaccharides, lipids, steroids, prostaglandins, prostacyclines, and nucleic acids (including DNA and RNA). As used herein, the term "protein" includes glycosylated and unglycosylated proteins. These and other terms and procedures are as defined in WO-A-9823950; see the sections headed "Biological samples", "Analysis of proteins" (twice), "Analysis of oligosaccharides", "Computer analysis of the detector output", "Computer generation and analysis of profiles", "Removal of selected portions of a supported gel", and "Processing removed portions of the gel".

In connection with the first "Analysis of proteins" section, a purification step is now introduced. A wide variety of purification techniques may be used in this first step. For example, purification may occur by the use of Fast Protein Liquid Chromatography (FPLC), ion exchange chromatography or affinity chromatography. Preferably FPLC is used, comprising one or more affinity columns containing affinity chromatography media which binds selectively the biomolecules of interest.

5. EXAMPLE

Proteins from Serum and Synovial Fluid of Patients with Rheumatoid Arthritis

Proteins in serum and synovial fluid from patients with rheumatoid arthritis (RA) were purified by FPLC, separated by isoelectric focusing followed by SDS-PAGE and compared.

5.1. FPLC Purification

Selected proteins which are desired to be specifically removed from the sample prior to proteome analysis e.g.

albumin, haptoglobin and transferrin present in serum were removed by a FPLC purification step. This was achieved by passing the biological sample through a series of Hi-trap affinity chromatography columns each comprising immobilised antibodies specific for a particular protein. The specific proteins bind to the column and the eluate is collected and concentrated by centrifugal ultrafiltration.

5.2. Isoelectric Focusing

For isoelectric focusing (IEF), each sample (after FPLC treatment) was applied to an Immobiline® DryStrip Kit (Pharmacia BioTech), following the procedure described in the manufacturer's instructions, see Instructions for Immobiline® DryStrip Kit, Pharmacia, #18-1038–63, Edition AB (incorporated herein by reference in its entirety), with optional modifications as described by Sanchez et al. 1997, Electrophoresis 18: 324–327 (incorporated herein by reference in its entirety).

In certain cases, in order to increase the resolution in a particular pH range or to load a larger quantity of a target protein onto the gel, a narrow-range "zoom gel" having a pH range of 2 pH units or less was used, according to the method described in Westermeier, 1993, Electrophoresis in Practice (VCH, Weinheim, Germany), pp. 197–209 (which is incorporated herein by reference in its entirety).

5.3. Gel Equilibration and SDS-PAGE

IEF gels were prepared for SDS-PAGE by equilibration in a SDS buffer system according to a two step procedure comprising initial reduction of the disulfide bonds, followed by alkylation of the free thiol groups, as described by Sanchez et al., id. Thereafter, SDS-PAGE was carried out according to Hochstrasser et al., 1988, Analytical Biochemistry 173: 412–423 (incorporated herein by reference in its entirety), with modifications as specified below.

5.4. Preparation of Supported Gels

Covalent attachment of SDS-PAGE gels to a glass support was achieved by applying a 0.4% solution of γ-methacryloxypropyltrimethoxysilane in ethanol to the glass plate ("the bottom plate") to which the gel was to be attached. Excess reagent was removed by washing with water, and the bottom plate was allowed to dry. At this stage, both as identification for the gel, and as a marker to identify the coated face of the plate, an adhesive bar-code was attached to the bottom plate in a position such that it would not come into contact with the gel matrix.

An opposing glass plate ("the top plate") was treated with RepelSilane (Pharmacia Biotech) to minimize gel attachment. After applying the reagent, the top plate was heated by applying a flow of heated air (e.g. from a hot air gun) to the surface of the plate. Excess reagent was again removed by water washing, and the top plate was allowed to dry.

The dried plates were assembled into a casting box with a capacity of 13 gel sandwiches. Several casting boxes can be assembled in parallel to cast more gels under the same conditions. The top and bottom plates of each sandwich were spaced by means of 1 mm thick spacers. The sandwiches were interleaved with acetate sheets to facilitate separation of the sandwiches after gel polymerization. Casting was then carried out according to Hochstrasser et al., op. cit.

5.5. SDS-PAGE

The gel strips from the IEF step were applied to the top of the poured SDS-PAGE gel and electrophoresis begun. In order to ensure even cooling of the gel during the electrophoresis run, a system was designed essentially as described by Amess et al,. 1995, Electrophoresis 16: 1255–1267 (incorporated herein by reference in its entirety). Even, efficient cooling is desirable in order to minimize thermal fluctuations during electrophoresis and hence to maintain the consistency of migration of the proteins. Electrophoresis was carried out until the tracking dye reached the bottom edge of the gel. The gels were then removed immediately for staining.

5.6. Staining

The top plate of the gel cassette was carefully removed, leaving the gel bonded to the bottom plate. The bottom plate with its attached gel was then placed into a staining apparatus, which has the capacity to accommodate 12 gels. The gels were completely immersed overnight in fixative solution, comprising 40% (v/v) ethanol, 10% (v/v) acetic acid, 50% (v/v) water. The fixative was then drained from the tank, and the gels were primed by immersion in 7.5% (v/v) acetic acid, 0.05% (w/v) SDS for 30 mins. The priming solution was then drained, and the gels were stained by complete immersion in the dye solution for 4 hours. A stock solution of fluorescent dye was prepared by diluting Sypro Red (Molecular Bioprobes, Inc., Eugene, Oreg.), according to the manufacturer's instructions. The diluted solution was filtered under vacuum though a 0.4 μm filter.

In order to achieve a continuous, even circulation of the various solutions over all 12 gels, solutions were introduced into the tank via a distribution bar, extending along the bottom of the tank across its entire width and provided with holes that allow the solution to flow evenly over each of the gels.

5.7. Imaging of the Gel

A computer-readable output was produced by imaging the fluorescently stained gels with a Storm scanner (Molecular Dynamics, Sunnyvale, Calif.) according to the manufacturer's instructions, (see Storm User's Guide, 1995, Version 4.0, Part No. 149–355, incorporated herein by reference in its entirety) with modifications as described below. Since the gel was rigidly bonded to a glass plate, the gel was held in contact with the scanner bed during imaging. To avoid interference patterns arising from non-uniform contact between the gel and the scanner bed, a film of water was introduced under the gel, taking care to avoid air pockets. Moreover, the gel was placed in a frame provided with two fluorescent buttons that were imaged together with the gel to provide reference points (designated M1 and M2) for determining the x,y coordinates of other features detected in the gel. A matched frame was provided on a robotic gel excisor in order to preserve accurate alignment of the gel. After imaging, the gels were sealed in polyethylene bags containing a small volume of staining solution, and then stored at 4° C.

The output from the scanner was first processed using MELANIE® to autodetect the registration points, M1 and M2; to autocrop the images (i.e., to eliminate signals originating from areas of the scanned image lying outside the boundaries of the gel, e.g. the reference frame); to filter out artifacts due to dust; to detect and quantify features; and to create image files in GIF format. Features were detected by a computer-mediated comparison of potential protein spots with the background to select areas of the gel associated with a signal that exceeded a given threshold representing background staining.

A second program was used for interactive editing of the features detected and to match duplicate gels for each sample. First, images were evaluated to reject images which had gross abnormalities, or were of too low a loading or overall image intensity, or were of too poor a resolution, or where duplicates were too dissimilar. If one image of a duplicate was rejected then the other image belonging to the duplicate was also rejected regardless of image quality. Samples that were rejected were scheduled for repeat analysis.

Landmark identification was used to correct for any variability in the running of the gel. This process involves the identification of certain proteins which are expected to be found in any given biological sample. As these common proteins exhibit identical isoelectric points and molecular weight from sample to sample, they can be used as standards to correct for any possible gel variation or distortion. The pI and molecular weight values for the landmarks in the reference gel were determined by co-running a sample with *E. coli* proteins which had previously been calibrated with respect to known protein in human plasma. Features which were considered to be artifacts, mainly at the edges of the gel image and particularly those due to the sample application point and the dye-front, were removed. Duplicate gels were then aligned via the landmarks and a matching process performed so as to pair identical spots on the duplicate gels. This provided increased assurance that subsequently measured isoelectric points and molecular weights were accurate, as paired spots demonstrated the reproducibility of the separation. The corrected gel, in addition to being used for subsequent analysis, was printed out for visual inspection.

Generation of the image was followed by computer measurement of the x,y coordinates of each protein, which were correlated with particular isoelectric points and molecular weights by reference to the known landmark proteins or standards. A measurement of the intensity of each protein spot was taken and stored. Each protein spot was assigned an identification code and matched to a spot on a master gel, i.e., a reference gel which contained most or all of the protein spots seen in each type of sample and was used as a template to which the protein spots of the other samples were matched. This step allowed for the identification of putative correlate spots across many different gels. The data collected during collection of the original biological sample, as described in section 5.1, were reunited with the gel data, thereby permitting the analysis of computer selected cross-sections of the samples based on information such as age or clinical outcome.

The end result of this aspect of the analysis was the generation of a digital profile which contained, for each identified spot: 1) a unique arbitrary identification code, 2) the x,y coordinates, 3) the isoelectric point, 4) the molecular weight, 5) the signal value, 6) the standard deviation for each of the preceding measurements, and 7) a pointer to the MCI of the spot on the master gel to which this spot was matched. By virtue of the LIMS, this profile was traceable to the actual stored gel from which it was generated, so that proteins identified by computer analysis of gel profile databases could be retrieved. The LIMS also permitted the profile to be traced back to the original sample or patient.

5.8. Digital Analysis of the Gel

Once the profile was generated, analysis was directed toward the selection of interesting proteins.

The protein features in the individual images from the paired serum and synovial fluid samples were compared electronically. Molecular identity of any one feature across the set of images is defined in this analysis as identity of position in the 2-D separation. Quantitative measurement of the abundance of an individual feature in an individual image was based on normalized fluorescence intensity measured for that feature in that image. Those proteins whose abundance differed between the sets of serum and synovial fluid samples were revealed by electronic comparison of all detected features in all relevant images.

5.9. Recovery and Analysis of Selected Proteins

Differentially expressed proteins were robotically excised and processed to generate tryptic peptides; partial amino acid sequences of these peptides were determined by mass spectroscopy, using de novo sequencing.

5.10 Results

These initial experiments identified 12 proteins that were present at higher levels in human RA synovial fluid than in matched serum samples, and 9 proteins that were present at lower levels in human RA synovial fluid than in matched serum samples. Partial amino acid sequences were determined for each of these differentially expressed proteins. Computer analysis of public databases revealed that 16 of these partially sequenced proteins were known in the art and that 5 were not described in any public database examined.

References herein to U.S. patent application Ser. No. 08/877,605 apply also to the International Patent Application No. PCT/GB98/01486. In addition, reference may be made to WO-A-9801749, for a discussion of techniques for the enhanced separation of species, e.g. in a gel.

What is claimed is:

1. A computer-assisted method for selecting and directing the isolation of one or more proteins present in a two-dimensional array, comprising:

a purification step, wherein a biological sample is treated by selectively depleting the sample of one or more proteins;

a first separation step following the purification step, wherein a plurality of proteins in the treated sample are separated according to a first physical or chemical property to form a one-dimensional array of proteins;

a second separation step, wherein the one-dimensional array of proteins is separated according to a second physical or chemical property to form the two-dimensional array;

imaging the two-dimensional array or a replica thereof to generate a computer-readable output comprising, for each of a plurality of proteins detected in the two-dimensional array, a pair of x,y coordinates and a signal value;

processing the output in at least one computer to select one or more of the detected proteins in accordance with previously ordained or operator-specified criteria; and generating machine-readable instructions that direct a robotic device to isolate at least one of the selected proteins from the two-dimensional array.

2. The method according to claim 1, in which the proteins include glycoproteins.

3. The method according to claim 1, wherein the purification step comprises selectively depleting the sample of a plurality of proteins.

4. The method according to claim 1, wherein the purification step comprises selectively depleting the sample of one or more proteins selected from the group consisting of albumin, immunoglobulins, haptoglobin and transferrin.

5. The method according to claim 4, wherein the purification step comprises selectively depleting the sample of a plurality of proteins selected from the group consisting of albumin, immunoglobulins, haptoglobin and transferrin.

6. The method according to claim 1, wherein the biological sample is serum.

7. The method according to claim 1, wherein the purification step comprises a protein-specific affinity method.

8. The method according to claim 7, wherein the purification step comprises affinity precipitation.

9. The method according to claim 7, wherein the purification step comprises affinity chromatography.

10. The method according to claim 7, wherein the purification step comprises Fast Protein Liquid Chromatography (FPLC).

11. The method according to claim 9, wherein the affinity chromatography employs one or more columns each comprising an immobilized antibody specific for a particular protein to be depleted.

12. The method according to claim 11, wherein the purification step depletes the biological sample of albumin, haptoglobin and transferrin.

13. The method according to claim 1, in which the proteins in the two-dimensional array have been separated by isoelectric focusing, followed by electrophoresis in the presence of sodium dodecyl sulfate.

14. The method according to claim 13, in which the two-dimensional array is contained in a polyacrylamide gel.

15. The method according to claim 14, in which the polyacrylamide gel is bonded to a generally planar solid support such that the gel has two-dimensional spatial stability, and the support is substantially non-interfering with respect to detection of a detectable label carried by the proteins.

16. The method according to claim 15, in which the polyacrylamide gel is covalently bonded to the solid support.

17. The method according to claim 15, in which the detectable label is a fluorescent label.

18. The method according to, claim 15, in which the solid support is glass.

19. The method according to any one of claims 1, 2, 3, 4, 5, 6, 7, 8, 9, 10, 11, 12, 13, 14, 15, 16, 17 or 18, further comprising isolating at least one of the selected proteins from the two dimensional array by means of the robotic device in accordance with the machine-readable instructions.

* * * * *